| (12) | United States Patent | (10) Patent No.: US 9,572,653 B2 |
|---|---|---|
| | Dardi | (45) Date of Patent: Feb. 21, 2017 |

(54) HYDROGEL JACKETED STENTS

(76) Inventor: Peter S. Dardi, Atlanta, GA (US)

( * ) Notice: Subject to any disclaimer, the term of this patent is extended or adjusted under 35 U.S.C. 154(b) by 241 days.

(21) Appl. No.: 13/269,863

(22) Filed: Oct. 10, 2011

(65) Prior Publication Data

US 2012/0089218 A1    Apr. 12, 2012

Related U.S. Application Data

(60) Provisional application No. 61/391,736, filed on Oct. 11, 2010.

(51) Int. Cl.
| *A61F 2/07* | (2013.01) |
| *A61F 2/88* | (2006.01) |
| *A61F 2/915* | (2013.01) |
| *A61F 2/844* | (2013.01) |
| *A61F 2/89* | (2013.01) |
| *A61F 2/958* | (2013.01) |
| *A61F 2/966* | (2013.01) |

(52) U.S. Cl.
CPC ............ *A61F 2/07* (2013.01); *A61F 2/88* (2013.01); *A61F 2/915* (2013.01); *A61F 2/844* (2013.01); *A61F 2/89* (2013.01); *A61F 2/958* (2013.01); *A61F 2/966* (2013.01); *A61F 2002/072* (2013.01); *A61F 2002/075* (2013.01); *A61F 2002/077* (2013.01); *A61F 2210/0004* (2013.01); *A61F 2210/0014* (2013.01); *A61F 2210/0057* (2013.01); *A61F 2210/0061* (2013.01); *A61F 2220/005* (2013.01); *A61F 2220/0058* (2013.01); *A61F 2250/0003* (2013.01); *A61F 2250/0067* (2013.01); *A61F 2250/0069* (2013.01); *A61F 2250/0098* (2013.01)

(58) Field of Classification Search
CPC ......... A61F 2210/0061; A61F 2/06–2002/007; A61F 2/24–2/2438; A61F 2/82–2/97
USPC ................................. 623/1.18–1.19
See application file for complete search history.

(56) References Cited

U.S. PATENT DOCUMENTS

| 4,886,062 A | * | 12/1989 | Wiktor ......................... 606/194 |
| 4,909,244 A | | 3/1990 | Quarfoot et al. |
| 5,674,241 A | | 10/1997 | Bley et al. |

(Continued)

OTHER PUBLICATIONS

"Crease", Collins English Dictionary, p. 1 of 1, accessed Dec. 11, 2013.*

(Continued)

*Primary Examiner* — Yashita Sharma
*Assistant Examiner* — Rebecca Preston
(74) *Attorney, Agent, or Firm* — Christensen Fonder Dardi; Peter S. Dardi

(57) ABSTRACT

Hydrogel jacketed stents provide the ability to fill in the stent frame in vivo to at least partially cover the interior of the surface of the stent following deployment while having the convenience of attaching the jacket to the exterior of the stent. The hydrogel can be pleated and/or folder over the exterior of the stent to provide for extension of the stent without damaging the hydrogel. The hydrogel sheet can be secured at one or more points along the circumference to associate the sheet of hydrogel with the exterior surface of the stent frame. The stent can be conveniently delivered using similar technology as conventional stents if desired. The hydrogel can provide for drug delivery if desired.

25 Claims, 3 Drawing Sheets

(56) References Cited

U.S. PATENT DOCUMENTS

| | | | |
|---|---|---|---|
| 5,902,329 A * | 5/1999 | Hoffmann | A61K 47/48992 |
| | | | 607/121 |
| 6,013,099 A * | 1/2000 | Dinh et al. | 623/1.15 |
| 6,106,530 A | 8/2000 | Harada | |
| 6,124,523 A | 9/2000 | Banas et al. | |
| 6,156,005 A | 12/2000 | Theron | |
| 6,364,894 B1 | 4/2002 | Healy et al. | |
| 6,491,617 B1 | 12/2002 | Ogle et al. | |
| 6,656,214 B1 * | 12/2003 | Fogarty et al. | 623/1.13 |
| 6,899,729 B1 * | 5/2005 | Cox et al. | 623/1.13 |
| 6,960,617 B2 | 11/2005 | Omidian et al. | |
| 7,083,646 B2 | 8/2006 | Valint, Jr. et al. | |
| 7,354,449 B2 | 4/2008 | Goodwin et al. | |
| 2002/0062147 A1 * | 5/2002 | Yang | 623/1.13 |
| 2003/0009213 A1 * | 1/2003 | Yang | 623/1.13 |
| 2003/0074049 A1 | 4/2003 | Hoganson et al. | |
| 2005/0004653 A1 * | 1/2005 | Gerberding et al. | 623/1.13 |
| 2006/0034883 A1 * | 2/2006 | Dang | A61F 2/07 |
| | | | 424/422 |
| 2006/0051338 A1 * | 3/2006 | Galloway et al. | 424/94.5 |
| 2006/0265049 A1 * | 11/2006 | Gray et al. | 623/1.16 |
| 2007/0179600 A1 | 8/2007 | Vardi | |
| 2008/0086110 A1 | 4/2008 | Galdonik et al. | |
| 2008/0132999 A1 * | 6/2008 | Mericle et al. | 623/1.34 |
| 2008/0140176 A1 * | 6/2008 | Krause et al. | 623/1.11 |
| 2008/0201007 A1 | 8/2008 | Boyden et al. | |
| 2009/0317442 A1 | 12/2009 | Banister et al. | |
| 2010/0094409 A1 * | 4/2010 | Barker | A61F 2/07 |
| | | | 623/1.46 |
| 2010/0324464 A1 | 12/2010 | Kamakura et al. | |
| 2012/0303116 A1 * | 11/2012 | Gorman et al. | 623/2.11 |

OTHER PUBLICATIONS

European Search Report from application No. EP 11 83 3191 dated Feb. 5, 2015 (9 pages).

Japanese office action from application No. 2013-533908 dated Aug. 25, 2015, with translation of office action summary (11 pages).

* cited by examiner

HYDROGEL JACKETED STENTS

CROSS REFERENCE TO RELATED APPLICATIONS

This application claims priority to copending U.S. provisional patent application 61/391,736 filed on Oct. 11, 2010, entitled "Hydrogel Jacketed Stents," incorporated herein by reference.

FIELD OF THE INVENTION

The invention relates to stents used to open up occlusions within a vessel within a patient, such as a blood vessel, generally an artery. In particular, the invention relates to stents with a hydrogel jacket over a frame that swells in vivo to at least partially surround the frame to reduce contact of the frame with the flow through the vessel. The invention further pertains to methods for forming and using the stent.

BACKGROUND OF THE INVENTION

Stents have found significant utility for facilitating the opening of clogged or narrowed vessels, such that the flow of blood or other biological fluid is restricted. In addition to blood vessels, stents have found utility for use in bile ducts, ducts of the reproductive system, and other similar vessels in the body. Of particular medical importance are coronary stents, which are placed in a coronary artery or other arteries to treat atheroscerosis. Stents used to open vessels generally have an elongate cylindrical structure with stent walls having an open construction that provides for tissue in growth around the stent frame. The stents are delivered in a low profile configuration and are extended out to the vessel within the patient either simultaneously or subsequently to a procedure to correspondingly expand the diameter of the vessel lumen. However, stents can be prone to restenosis, due to an inflammatory response induced by the foreign object in the body. In other words, in some cases thrombus formation or the like can take place at the site of the stent.

To reduce restenosis, polymer coatings have been used to coat stents, and the coatings generally are drug eluting. The coatings generally comprise a hydrophilic polymer that is coated over the frame elements. The coated stents maintain an open structure of the frame. Coated stents have met with considerable success commercially. However, studies have suggested cracking of the polymer coating that has been linked in studies with deleterious effects to the patient.

SUMMARY OF THE INVENTION

In a first aspect, the invention pertains to jacketed stent for placement in a bodily vessel comprising an extendable stent frame having an exterior surface defined by the stent frame and a hydrogel sheet associated with the exterior surface of the scaffold such that the hydrogel forms a jacket over the stent frame upon extension of the stent frame to its extended configuration. In some embodiments, the hydrogel sheet can have a thickness and expansion in an aqueous fluid such that the expanded hydrogel sheet at least partially covers the inner surface of the extended stent in an aqueous environment. A medical device can comprise a delivery catheter, a delivery actuator supported by the delivery catheter and the jacketed stent operably connected with the delivery actuator to control deployment of the stent in a vessel.

In a further aspect, the invention pertains to a jacketed stent comprising a stent frame having an outer surface and a hydrogel sheet associated with the outer surface of the stent frame. In some embodiments, the hydrogel sheet is folded to accommodate a larger surface area of the hydrogel sheet relative to the outer surface of the stent frame and wherein the stent frame extends to a deployed configuration with the hydrogel sheet stretched along the outer surface of the stent frame.

In additional aspects, the invention pertains to a jacketed stent comprising a stent frame and a hydrogel sheet. The stent frame can have an open structure, an outer surface, and an extended configuration with a diameter at least about a factor of two greater than its initial configuration. The hydrogel sheet can be associated with the outer surface of the stent frame, and in some embodiments the hydrogel sheet hydrates to an expanded form with a thickness at least about 1.5 greater than its initial thickness.

In another aspect, the invention pertains to a method of forming a hydrogel jacketed stent, the method comprising securing a hydrogel sheet over an extendable stent frame in a low profile configuration, in which the hydrogel is structured to provide for expansion in diameter by at least of the stent frame by a factor of at least about 2 and in which the hydrogel expands upon hydration to a thickness at least about 1.5 times the initial thickness of the sheet. The hydrogel jacket can be folded and/or pleated around the stent frame in an un-deployed configuration such that the hydrogel jacket unfolds when deployed.

Furthermore, the invention pertains to a method for the delivery of a hydrogel jacketed stent comprising extending the stent to an extended configuration within the lumen of a vessel within a patient, wherein the stent comprises an open structured stent frame having an outer surface and a hydrogel jacket associated with the outer surface. In some embodiments, the extended stent has the hydrogel jacket secured between the vessel wall and the stent frame such that the hydrogel hydrates and expands to fill the open portions of the stent frame after sufficient time to provide for hydration of the hydrogel.

DETAILED DESCRIPTION OF THE INVENTION

Figure 1:
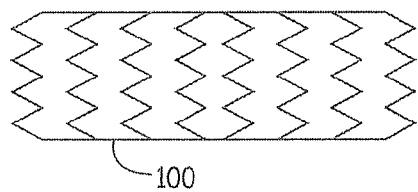
FIG. 1 is a side plan view of a stent frame.

New stent designs have been developed that use a jacket of a hydrogel over an open scaffolding of the stent, such as a conventional stent frame. The hydrogel can function effectively as an alternative to a coating that is designed to avoid cracking, peeling or the like. The hydrogel can be selected to have reasonable elastic properties and expansion upon contact with aqueous liquid. The use of a jacket of expanding hydrogel addresses a range of issues in an effective and practical way with the potential of significantly improved clinical results. Even with significant elasticity, the hydrogel may not be able to accommodate the large expansion associated with stent deployment. However, the hydrogel can be pleated, folded or otherwise placed over the un-deployed stent so that the jacket opens up or unfolds to accommodate the expanding dimension of the stent allowing for more modest elasticity of the hydrogel. Expansion of the hydrogel jacket over the expanded stent can result in the hydrogel expanding through and around the open stent structure, and the expanded hydrogel may form an effective lining of the stent from an initially unlined structure. Through the expansion of the hydrogel, edges associated with the stent structure can be smoothed with the hydrogel polymer to reduce the incidence of thrombus formation as well as restenosis. Also, the hydrogel can be a very effective drug delivery system providing for the possibility of the controlled release of a significant quantity of a selected drug or drugs.

Stents have been used effectively to support the opening of blood vessels at occlusions for mammalian patients, especially human patients. For example, stents have been used in coronary arteries, carotid arteries, saphenous vein grafts, other blood vessels as well as other vessels, such as bile ducts, vessels of the urinary track, vessels of the reproductive track and the like. Stents generally have an approximately cylindrical shape with a structure having open walls. The stent generally is delivered in a narrow profile, and the stent can be deployed with a balloon or the like. In some embodiments, the stent is self extending, such as following release of the stent from a sheath or the like. The stent upon deployment generally increases very significantly in diameter. For example, the stent can be formed from a suitable material that is elastic and/or has a shape memory such that the stent material can expand as designed without breaking or excessively weakening. Due to this significant structural changes corresponding with stent delivery, significant forces are imposed on coatings during the deployment of the stent, and studies have suggested that some stents coatings that are drug eluting may be susceptible cracking of the coating. Regardless, the jacketed stents herein provide significant potential advantages since the material is not constrained as a coating.

The jacketed stents described herein comprise a stent frame and a jacket over the exterior of the stent frame. The jacket comprises a hydrogel. Generally, the stent frame can have any reasonable uncoated or coated stent design, such as existing designs. Stent frames can have an open design of interconnected struts arranged in a generally cylindrical shape. Commercial stents have been formed of resilient metal, although polymer stents have been proposed.

Stents may be, for example, balloon extendable, self-extendable or extendable using any other reasonable mechanism. Balloon extendable stents can be crimped to the balloon for delivery. Some balloon-stent structures are described further, for example, in U.S. Pat. No. 6,106,530, entitled "Stent Delivery Device," U.S. Pat. No. 6,364,894, entitled "Method of Making an Angioplasty Balloon Catheter," and U.S. Pat. No. 6,156,005, entitled "Ballon [sic] Catheter For Stent Implantation," each of which are incorporated herein by reference.

Stents and balloons associated with therapeutic agents are described further in U.S. Pat. No. 6,491,617 to Ogle et al., entitled "Medical Articles That Resist Restenosis," incorporated herein by reference. Drug coated stents have been sold commercially. Examples of commercial coronary stents include, Cypher™ from Cordis/Johnson & Johnson, which has a coating that elutes sirolimus from a PEVA and PBMA, Taxus™ from Boston Scientific, which has a coating that elutes paclitaxel from SIBS copolymer coating and Endeavour™ from Medtronic, which has a coating that elutes zotarolimus from phophorylcholine. These particular coated stents are for coronary use.

The jacket for the stent comprises a hydrogel that covers the exterior of the stent or a portion thereof. A hydrogel is a non-soluble hydrophilic polymer. Generally, a hydrogel is crosslinked to introduce the non-soluble feature. Due to the hydrophilicity, hydrogels generally swell when in contact with an aqueous solvent. Hydrogels can be formulated to be biocompatible for placement in a patient.

Hydrogels of particular interest can exhibit significant swelling with contact with an aqueous solution. In particular, the hydrogel can swell at least about 50% in volume, and in some embodiments at least about 100% relative to an initial volume. Thus, the swelling hydrogel can expand to file the spaces between structural elements of the stent, especially when the stent is deployed with the hydrogel wedged between the vessel wall and the stent frame. Thus, the expanding hydrogel can effectively remove the edges of the stent structure from contact with the blood flow to reduce surfaces that can induce thrombosis.

The hydrogel should have reasonable mechanical strength so that the hydrogel is not significantly damaged during expansion of the stent. In some embodiments, the hydrogel jacket can stretch a factor of two in diameter without rupturing. Correspondingly, in some embodiments, the hydrogel can be relatively elastic so that the hydrogel can expand somewhat during expansion of the stent. Suitable elastic hydrogels are described in U.S. Pat. No. 6,960,617 to Omidian et al. (the '617 patent), entitled "Hydrogels Having Enhanced Elasticity and Mechanical Strength Properties," and published U.S. patent application 2009/0317442 to Banister et al. (the '442 application), entitled "Super Elastic Epoxy Hydrogel," both of which are incorporated herein by reference. The '617 patent further discusses drug elution from hydrogels.

If the stent does not expand at deployment disproportionally to the expansion ability of hydrogel, then the hydrogel can be wrapped directly along the outer surface of the stent frame at delivery into the patient's vessel. However, in some embodiments, the hydrogel is not able to expand to the extent in which the stent expands. For these embodiments, the hydrogel can be placed around the stent such that the hydrogel unfolds upon deployment of the stent such that the hydrogel is jacketed in a stretched configuration over the exterior of the extended stent. For example, the hydrogel jacket can be pleated or wrapped over the exterior of the initial stent configuration. Once the stent is deployed into the extended configuration, the hydrogel swells as the hydrogel hydrates. The swelled hydrogel can be designed to expand through the openings in the wall of the stent to extend into the interior of the stent. Following expansion of the hydrogel, the swollen hydrogel may effectively form a coating along the interior of the stent within the vessel.

While it is generally desirable to limit the overall thickness of the deployed stent, the overall volume of the hydrogel jacket can be significantly greater than a stent coating since the thickness can be slightly greater and since the hydrogel fills the spaces between the structural elements of the stent. The hydrogel can be loaded with a drug that elutes into the vessel in a controlled fashion. Due to the larger volume of the hydrogel relative to a coating, a greater amount of drug can be effectively delivered than is practical with a coating. Also, hydrogels can be designed to control the release of the drug in a selected fashion based on experience with hydrogels. The drugs that elute form the hydrogels can include drugs that current elute from stent coatings, similar drugs, other drugs can be desirably delivered or combinations thereof.

When fully hydrated, the hydrogel swells, and the swelling can generally involve the hydrogel at least partially enveloping the stent frame. Depending on the degree of swelling and the hydrogel thickness, the hydrogel can have differing degrees of enveloping the stent frame. This enveloping of the stent frame by the swelling hydrogel can reduce the contact of blood with the stent frame along the interior of the stent. Thus, the hydrogel initially placed on the outside of the stent can improve the interface of the stent with the blood flow within the interior of the stent due to the swelling of the hydrogel. Thus, the hydrogel can reduce any incidence of embolism formation due to the presence of the stent in the vessel.

To form the hydrogel coated stent, a sheet of hydrogel with the selected dimensions can be associated with the unextended stent. The hydrogel can be placed over the stent frame . . . . For example, the hydrogel can be manipulated in a moist condition in which it is very pliable, and then dried into the formed low profile configuration for delivery.

Stent Structure and Materials

The hydrogel jacketed stents provide for appropriate expansion of the stents while also providing a cover for the stent frame. The hydrogel jacket can be attached over the exterior of the stent in a way to provide for expansion of the stent without resulting in significant damage to the hydrogel jacket during stent deployment. In particular, if the expansion of the stent is not too large and the hydrogel is sufficiently compliant, the hydrogel can be wrapped over the unextended stent frame such that it expands sufficiently to cover the extended stent following deployment without significantly ripping. In further embodiments, the jacket can be pleated, folded, wrapped or otherwise attached such that the hydrogel jacket can at least partially unfurl, possibly with some stretching, when the stent is deployed. Swelling of the hydrogel jacket over the stent frame can provide for at least some encapsulation of the stent frame to reduce or eliminate contact of the flow through the vessel with the stent frame. Sufficient swelling of the hydrogel can result in effective covering of the stent from with the use of only a cover or jacket of hydrogel. In some embodiments the hydrogel can elute a selected drug or combination of drugs.

The stent can be appropriately sized for the particular use of the stent. For example, for placement in coronary arteries, the stents generally have an expanded diameter of about 2 mm to about 5 mm, and other ranges can be suitable for other arteries or other vessels, such as from about 1 mm to about 50 mm. In general, the ratio of the stent diameter following deployment divided by the stent diameter prior to deployment is at least about 1.5, in further embodiments from about 2 to about 6 and in additional embodiments from about 2.25 to about 5. For many applications, the stent can have a length from about 10 mm to 100 mm or more. Generally, a stent product is distributed with a selection of a few sizes for selection of the more appropriate size for a particular vessel in the procedure. The structure of the stent frame can be designed with a generally cylindrical open shape with a woven, bent, molded, coiled, formed or similar open structure of struts, beam, supports or the like that adjusts accordingly to accommodate the significant change in diameter without breaking. A large variety of stent structures are known in the art, which can be adapted for placement of a hydrogel jacket, and new stent designs may be developed in the future. In some embodiments, the hydrogel jacket can have a dry thickness from about 0.001 millimeters (mm) to about 0.5 mm, in other embodiments from about 0.0025 mm to about 0.25 mm, and in further embodiments from 0.005 mm to about 0.1 mm. A person of ordinary skill in the art will recognize that additional ranges of hydrogel thickness within the specific ranges above are contemplated and are within the present disclosure.

Stent frames are generally cylindrical, although the stent frame can have tappers or the like. Also, the stent frame when extended can adjust to the shape of the vessel, which can have irregularities or the like. Stent frames can be formed from, for example, stainless steel, tantalum, shape memory alloys, polymers and coated versions thereof. Suitable shape memory alloys include, for example, Nitinol®, a nickel-titanium alloy, cobalt alloys, such as Elgiloy®, a cobalt-chromium-nickel chromium-nickel alloy, MP35N, a nickel-cobalt-chromium-molybdenum alloy, or combinations thereof. Shape memory metals can be used to form self extending stents which extend upon heating, such as to body temperature. Biocompatible polymers are known in the art, and suitable polymers can be bioresorbable. Gold, platinum and/or other radiopaque materials can be used for the stent or a portion thereof to facilitate imaging to facilitate placement of the device in the patient. For example, the stent can be gold plated at its ends to provide enhanced visualization with x-rays.

Various hydrogels have found use in medical applications. Hydrogels generally comprise soluble or hydroscopic polymers that are crosslinked to form to form an insoluble polymer material, although applicant does not want to be limited by particular polymer structure. Hydrogels are insoluble hydrophilic polymers that swell with water in an aqueous environment when contacting an aqueous liquid such that water dispersed through the polymer matrix comprises a significant fraction, and possibly a majority, of the weight of the material in the hydrated form. As noted above, the '617 patent and the '442 application describe specific hydrogels with desirable mechanical properties for use as a hydrogel jacket on a stent. A range of hydrogels have been described in the context of wound healing applications, and some of these hydrogels are suitable for formation of hydrogel jackets.

Suitable polymers compositions for the hydrogel include, for example, polyurethanes, polyacrylic acid and esters thereof, polymethacrylic acid and esters thereof, polyacrylonitrile, cellulose and derivatives thereof, polyethylene glycol and derivatives thereof, polyacrylamide, epoxy polymers, copolymers thereof and mixtures thereof. Crosslinked dendrimer polymers and other highly branched polymers have been proposed for the formation of superelastic epoxy polymers in the '422 application. Hydrogel materials for wound dressings that can be adapted for forming a hydrogel stent jacket are described, for example, in U.S. Pat. No. 4,909,244 to Quarfoot et al., entitled "Hydrogel Wound Dressing," and published U.S. patent application 2010/0324464 to Kamakura et al., entitled "Wound-Covering Hydrogel Material," both of which are incorporated herein by reference.

The hydrogel can be delivered with a drug or other therapeutic agent that gradually elutes from the hydrogel within the patient. Suitable therapeutic agents include, for example generic material, such as DNA fragments, DNA vectors, plasmids, RNA or the like. Suitable drugs include, for example, anti-thrombogenic agents, anti-proliferative agents, anti-inflammatory agents, growth factors, growth factor receptor agonists, growth factor inhibitors, cholesterol lowering agents, vasodilating agents, antibiotics, hormones, fibrinolytic agents and the like. Suitable time release agents, such as those known in the art can be used if desired. Therapeutic agents can also be delivered with suitable additives.

Figure 2:
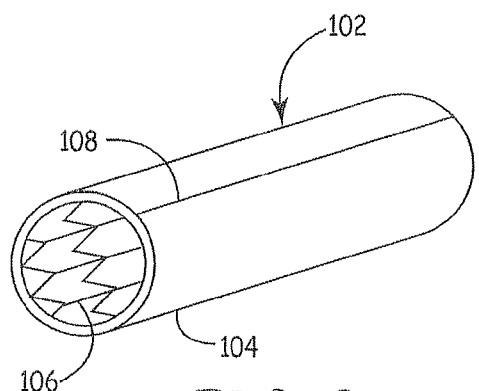
FIG. 2 is a perspective side view of a stent with a hydrogel jacket over a stent frame.

Referring to FIG. 1, a stent frame 100 is shown schematically comprising extendable struts that can extend with the application of force or self-extending in response to release or resistance or application of heat to body temperature. An embodiment of a hydrogel jacketed stent is 102 shown in FIG. 2 in which a hydrogel jacket 104 is wrapped around a stent frame 106 to form jacketed stent 102. Hydrogel jacket 104 can be secured with an optional attachment seam 108 that may or may not bind hydrogel jacket 104 to stent frame 106. The seam corresponds with a point of attachment along the circumference of the stent frame, and such a seam may or may not extend along the entire length of the interface between the hydrogel jacket and the stent frame.

Figure 3:
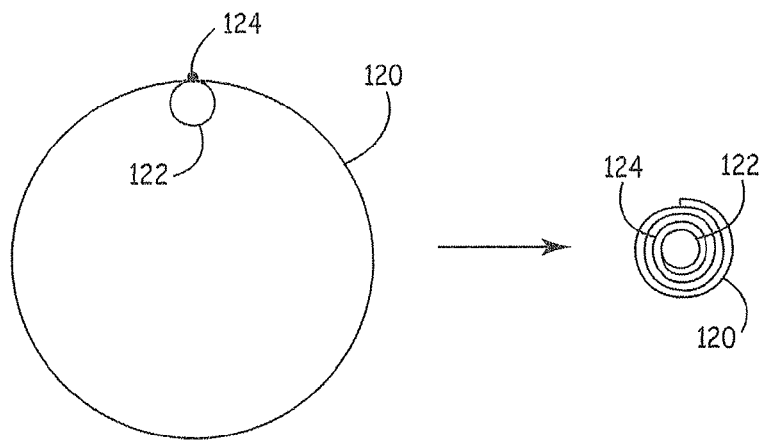
FIG. 3 is an end plan view of a stent frame with an attached hydrogel sheet, which is wound around the stent frame in the right view with an arrow indicating the winding process.

Referring to FIG. 3, in some embodiments, a hydrogel sheet 120 can be secured to a stent frame 122 at an attachment seam 124. The seam can be formed, for example, with a biocompatible adhesive, through embedding the stent frame along the seam into the hydrogel sheet, heat bonding or any other suitable technique. If the hydrogel is sufficiently flexible, hydrogel sheet 120 can be wrapped over stent frame 122, as shown in the right view of FIG. 3. The rolling or wrapping process is indicated in FIG. 3 with an arrow. The free edge of the rolled hydrogel can be optionally kept in place prior to deployment with a relatively weak adhesive, with drying to make the sheet less flexible, with mechanical securing of the sheet, combinations thereof or the like.

The hydrogel may be sufficiently flexible for processing, such as the rolling process of FIG. 3, in a dry state, or some hydration, such as partial hydration, an be used to increase the flexibility of the hydrogel for processing. In appropriate embodiments, with the sheet rolled around stent frame, or otherwise positions as desired the hydrogel can be dried to hold the hydrogel in place in a low profile configuration. In alternative embodiments, the hydrogel can be maintained during storage and distribution in a partially hydrated state using appropriate packaging to control drying of the hydrogel. When the stent is delivered into the patient, the hydrogel begins to fully hydrate. When the hydrogel swells to full hydration, the hydrogel jacket swells to at least partially surround the stent frame. A sheath can be used to control hydration which may or may not be desirable to take place when the stent is placed into the patient or closer to the time of deployment. With respect to the embodiment in FIG. 3, the stent can be deployed with the hydrogel jacket unrolling, unfolding, stretching and/or the like due to its pliability or flexibility to be secured between the vessel wall and the stent frame in the deployed configuration.

Figure 4:
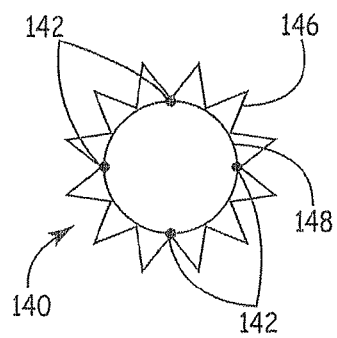
FIG. 4 is an end plan view of a stent frame with a pleated hydrogel jacket attached to the frame at selected points of the pleated jacket.
Figure 5:
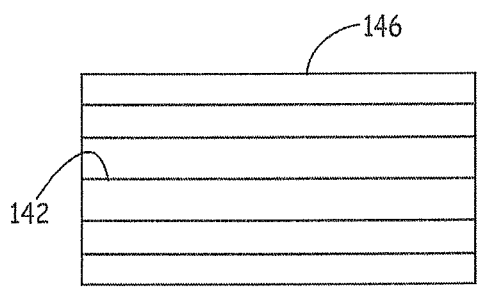
FIG. 5 is a side plan view of the hydrogel jacketed stent of FIG. 4 with a pleated hydrogel jacket.
Figure 6:
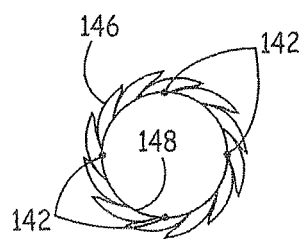
FIG. 6 is an end plan view of the hydrogel jacketed stent of FIG. 4 in which the pleats have been folded over to reduce the profile of the jacketed stent.

A pleated embodiment of a hydrogel jacket is shown in FIGS. 4 and 5. A hydrogel sheet can be pleated in a dry, partially hydrated or hydrated state to have sufficient flexibility for forming the pleats. As shown in FIG. 4, hydrogel jacketed stent 140 has four attachment seams 142 securing hydrogel sheet 146 to stent frame 148, but a greater or lesser number of attachment seams can be used. Referring to FIG. 6, pleated hydrogel sheet 146 can be folded over stent frame 148 to form a low profile configuration for delivery. The hydrogel pleats unfold when the stent is delivered in the vessel and the jacketed stent is extended when deployed.

Figure 7:
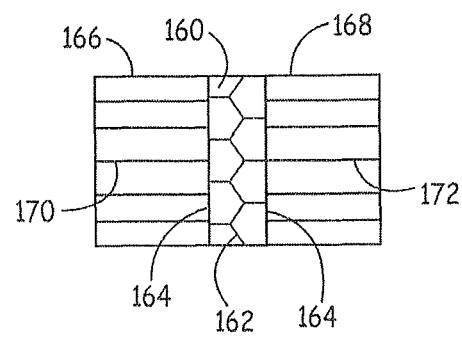
FIG. 7 is a side plan view of a hydrogel jacketed stent in which a portion of the stent frame is exposed by limited coverage of the hydrogel jacket. Radiopaque markers indicate the edges of the hydrogel jacket over the stent frame.

The hydrogel jacket may or may not cover the entire stent frame. For example, as shown in FIG. 7, a section 160 toward the middle of the stent frame 162 is not covered. In the embodiment of FIG. 7, edges of section 160 have radiopaque marker bands 164. As shown in FIG. 7 covered sections 166, 168 have pleated hydrogel sheets secured with attachment seems 170, 172. The number, size and locations of gaps in the hydrogel jacket or cover can be selected as desired. In some embodiments, the gap can be located at an edge of the stent frame. Expansion of the hydrogel from swelling can facilitate covering of the ends of the stent frame upon full hydration of the hydrogel although the hydrogel prior to delivery of the stent may not cover the ends of the stent fame. The longitudinal length of the stent frame may change slightly when the stent is deployed, and the placement of the hydrogel jacket can account for this change in length. Also, a gap in the jacket can allow for placement of the stent while providing for flow through a section of the jacket for example to provide flow for a branch vessel. In some embodiments, radiopaque bands can be placed to mark the gap in the jacket to provide for positioning of the gap.

Figure 9:
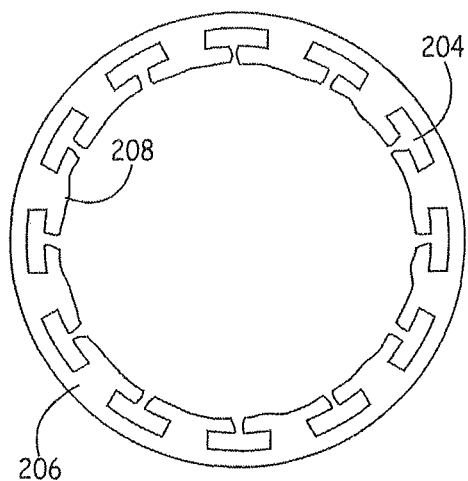
FIG. 9 is a sectional view of the deployed stent of FIG. 8 taken along line 9-9 of FIG. 8. For convenience, the vessel wall is not shown in the view.
Figure 8:
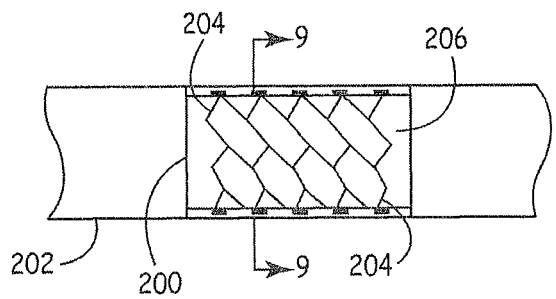
FIG. 8 is a sectional side view of a deployed hydrogel jacketed stent within a vessel of the body in which the hydrogel jacket has expanded from hydration to at least partially cover the interior surface of the stent frame. The section being taken through the center of the vessel.

Upon contact of the hydrogel jacketed stent with the fluid of the vessel within the patient, the hydrogel proceeds to fully hydrate. Referring to FIG. 8, a hydrogel jacketed stent 200 is shown deployed in a vessel 202. Hydrogel jacketed stent 200 comprises stent frame 204 and hydrogel jacket 206. As the hydrogel expands due to hydration while the hydrogel is positioned between the expanded stent frame and the vessel wall, the expanding hydrogel generally expands around the stent frame. A cross sectional view is shown schematically in FIG. 9 showing the expanded section of the hydrogel 208 along the interior and generally around the stent frame. Depending on the degree of expansion, the expanded hydrogel jacket can cover varying amounts of the stent frame. Thus, the stent frame is generally at least partially shielded from the blood flow, and the hydrogel can expand to form an effective interior coating of the stent frame in vivo following deployment of the hydrogel jacketed stent. In some embodiments, the hydrogel can then gradually elute one or more selected drugs.

Figure 10:
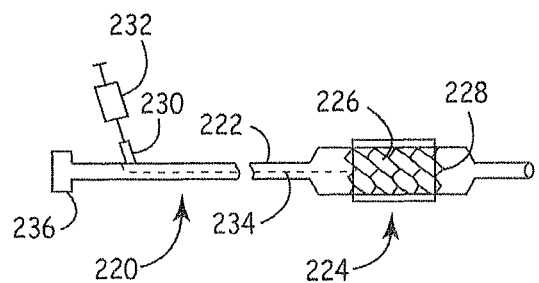
FIG. 10 is a fragmentary side plan view of a medical device with a deployment catheter having a mounted hydrogel jacketed stent positioned for deployment with the catheter. A portion of the catheter length is deleted for convenience.

Referring to FIG. 10, medical device 220 comprises a delivery catheter 222 and a hydrogel jacketed stent 224. As shown in FIG. 10, hydrogel jacketed stent 224 has a hydrogel jacket 226 over a stent frame 228, in which distal and proximal ends of stent frame 228 extend slightly past the edges of the hydrogel jacket in the un-deployed configuration. Delivery catheter 222 further comprises a fitting 230 for attachment of a fluid source 232 that can be connected to provide fluid through fluid lumen 234 (phantom lines) for the expansion and deflation of the balloon. The proximal end of delivery catheter 222 can have a fitting 236, such as a Luer fitting, to provide for access to a central lumen through a valve or the like connected at the fitting that can be used to track delivery catheter 222 over a guidewire or the like.

Figure 11:
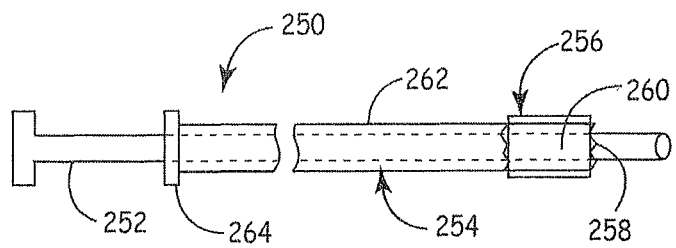
FIG. 11 is a fragmentary side view of a delivery catheter loaded with a hydrogel jacketed stent for delivery and a sheath extending over the catheter and the stent.

A sheath can be used to cover a hydrogel jacked stent for delivery. The sheath can be used to control expansion of a self extending stent, to protect the stent from damage or dislocation, to control hydration of the hydrogel, combinations thereof or for other purposes. The sheath can be withdrawn to expose the stent at an appropriate time of the procedure, such as when the sheath is at the desired deployment location in the patient's vessel. Referring to FIG. 11, an embodiment of a treatment system 250 is shown with a delivery catheter 252 and a sheath 254. Delivery catheter 252 comprises a jacketed stent 256 having a stent frame 258 and a hydrogel jacket 260. Delivery catheter 252 can comprise appropriate delivery structures to extend jacketed stent 256, or the stent can be self extending. Sheath 254 comprises a tubular element 262 and optionally a handle 264. Handle can be used to facilitate the sliding of sheath 254 over the outer surface of catheter 252.

For distribution, a hydrogel jacketed stent can be packaged loaded onto a delivery catheter and placed in a sterile wrapper, envelope or the like. Based on the properties of the hydrogel, the hydrogel jacketed stent can be distributed with the hydrogel dried or partially hydrated. If the hydrogel is partially hydrated, the hydrogel jacketed stent can be wrapped in a water tight wrapping that is removed shortly prior to use. The devices can be distributed with proper instruction to properly trained health care professionals.

The hydrogel associated with the deployed stent can provide a desirable surface for contacting the tissue of the vessel as well as the blood flow. Similarly, the hydrogel can provide a suitable environment for the colonization of native cells. The hydrogel can be infused with a desired drug or other compound to provide an improved vascular state at the stent and downstream.

Use of the Jacketed Stent

In general, the delivery of the hydrogel jacketed stent can be performed very similarly to the delivery of a conventional stent. The distal end of the delivery catheter is introduced into the patient, for example, with the use of one or more of hemostatic valves, fittings, introducers, guide catheters and the like. The stent then can be positioned in the vicinity of a constriction in the vessel. The delivery of the stent can be achieved with extension a balloon or other mechanical expanding element with appropriate actuation, or with the release of a self-extending device from a sheath or other constraint. The particular extension forces and speed of extension can be selected to be appropriate for the stent frame as well as the hydrogel jacket. In some embodiments, the hydrogel jacketed stent can be exposed to the fluid of the vessel for a period of time prior to stent deployment to provide for additional hydration of the hydrogel prior to deployment.

Figure 12:
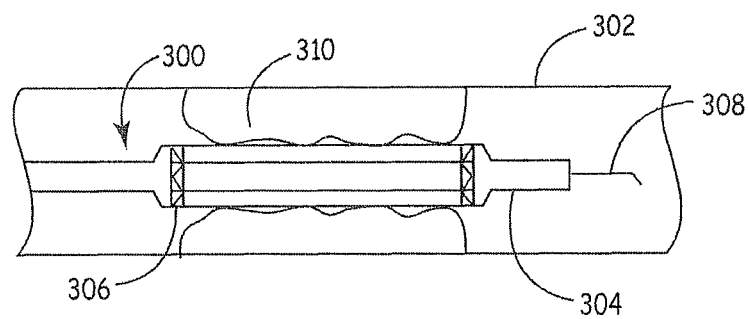
FIG. 12 is a fragmentary side view of a delivery catheter with a hydrogel jacketed stent positioned in a vessel at a selected location for the delivery of the stent.
Figure 13:
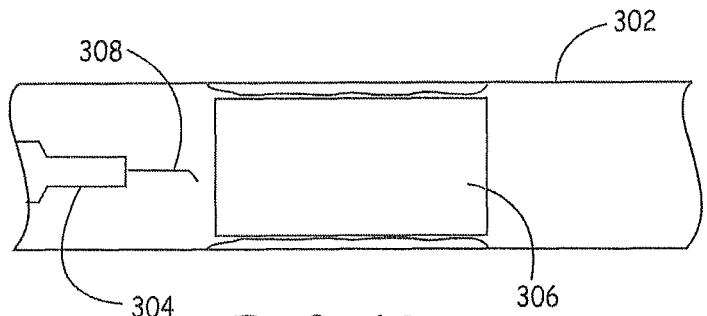
FIG. 13 is a fragmentary side view of the vessel of FIG. 12 following delivery of the hydrogel jacketed stent and the partial removal of the delivery catheter.

Referring to FIG. 12, a schematic side view is depicted of the distal end of a stent delivery device 300 within a vessel 302. The stent delivery device comprises a delivery catheter 304 and a hydrogel jacketed stent 306. The delivery catheter is positioned over a guidewire 308. The hydrogel jacketed stent is positioned at a narrowing of the vessel 310. FIG. 13 depicts the vessel after the deployment of hydrogel jacketed stent 306 and with partial withdrawal of delivery catheter 304. The blockage of the vessel 302 is decreased or eliminated following treatment and stent deployment. After deployment of the hydrogel jacketed stent 306, the delivery catheter can be removed from the patient and the vessel access point sealed with the stent remaining in place in the vessel.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

What is claimed is:

1. A jacketed stent for placement in a bodily vessel comprising a stent frame having an inner surface, an exterior surface, an extended configuration and an un-extended diameter, the jacketed stent having a hydrogel sheet associated with the exterior surface such that the hydrogel sheet forms a tubular jacket over and around a circumference of the stent frame upon extension of the stent frame to its extended configuration, wherein the stent frame is non-self extendable, wherein the hydrogel sheet has a thickness and comprises polyurethanes, polyacrylic acid and esters thereof, polymethacrylic acid and esters thereof, polyacrylonitrile, polyethylene glycol and derivatives thereof, polyacrylamide, epoxy polymers, copolymers thereof or mixtures thereof, wherein the hydrogel sheet is configured to swell when placed in water to a swollen state in which the hydrogel sheet at least partially covers the inner surface of the stent frame in the extended configuration in water and wherein the jacketed stent has an open inner lumen and wherein the hydrogel sheet has an un-hydrated thickness from 0.05 mm to 0.3 mm.

2. The jacketed stent of claim 1 wherein the ratio of an extended diameter of the stent frame in the extended configuration to the un-extended diameter of the stent frame is from about 2 to about 6.

3. The jacketed stent of claim 1 wherein the stent frame has an open wall.

4. The jacketed stent of claim 1 wherein the stent frame comprises a metal.

5. The jacketed stent of claim 1 wherein the hydrogel sheet swells by a factor of at least about 1.5 in thickness relative to its un-hydrated thickness upon exposure to the water.

6. The jacketed stent of claim 1 wherein the hydrogel sheet covers the exterior surface of the stent frame except for a portion at the ends of the stent frame.

7. The jacketed stent of claim 1 wherein the hydrogel sheet does not cover a portion of the stent frame and the jacketed stent further comprising radiopaque markers indicating the uncovered portion of the stent frame.

8. A medical device comprising a delivery catheter, a delivery actuator supported by the delivery catheter and a jacketed stent of claim 1 operably connected with the delivery actuator to control deployment of the jacketed stent in a vessel.

9. The medical device of claim 8 wherein the delivery actuator comprises a balloon that is positioned on the deliver catheter such that expansion of the balloon expands the jacketed stent, and wherein the delivery catheter further comprises a balloon flow channel operably connected to a fluid reservoir such that fluid from the reservoir can be transported in a controlled way to expand the balloon.

10. A medical device comprising the jacketed stent of claim 1, a delivery catheter and a sheath that slides relative to the delivery catheter and wherein the sheath has a configuration in which the jacketed stent is constrained between the deliver catheter and the sheath and a configuration in which the jacketed stent is unconstrained.

11. The jacketed stent of claim 1 wherein the hydrogel sheet in the swollen state covers the entire exterior surface of the stent frame.

12. The jacketed stent of claim 1 wherein the hydrogel sheet forms a cylinder.

13. The jacketed stent of claim 1 wherein the hydrogel sheet is free of folds and is attached at specific points of attachment.

14. The jacketed stent of claim 1 wherein the hydrogel sheet is free of folds and is dried onto the stent frame.

15. A jacketed stent comprising a stent frame having an outer surface, an inner surface and an un-extended diameter, the jacketed stent having a hydrogel sheet associated with the outer surface of the stent frame, wherein the hydrogel sheet is folded to accommodate a larger surface area of the hydrogel sheet relative to the outer surface of the stent frame and comprises polyurethanes, polyacrylic acid and esters thereof, polymethacrylic acid and esters thereof, polyacrylonitrile, polyethylene glycol and derivatives thereof, polyacrylamide, epoxy polymers, copolymers thereof or mixtures thereof and wherein the stent frame deploys to an extended configuration with the hydrogel sheet stretched along the outer surface of the stent frame and wherein the hydrogel sheet has a dry thickness from about 0.05 mm to about 0.3 mm and wherein the hydrogel sheet is configured to swell when placed in water.

16. The jacketed stent of claim 15 wherein the hydrogel sheet is pleated.

17. The jacketed stent of claim 15 wherein the hydrogel sheet is wrapped around the stent frame.

18. The jacketed stent of claim 15 wherein the hydrogel sheet is secured along a point on a circumference of the stent frame.

19. The jacketed stent of claim 15 wherein the hydrogel sheet is secured along a plurality of points on a circumference of the stent frame.

20. The jacketed stent of claim 15 wherein the extended configuration has an extended diameter and wherein a ratio of the extended diameter of the stent frame to the un-extended diameter of the stent frame is from about 2 to about 6.

21. The jacketed stent of claim 15 wherein the hydrogel sheet swells by a factor of at least about 1.5 in thickness relative to its dry thickness upon exposure to water.

22. The jacketed stent of claim 15 wherein the hydrogel sheet has a dry thickness from about 0.05 mm to about 0.3 mm.

23. The jacketed stent of claim 15 wherein the jacketed stent has an open central lumen.

24. The jacketed stent of claim 15 wherein the hydrogel sheet following hydration covers the outer surface of the stent frame over its entirety.

25. The jacketed stent of claim 15 wherein the hydrogel sheet is configured to swell when placed in water to a swollen state in which the hydrogel sheet at least partially covers the inner surface of the stent frame in the extended configuration.

* * * * *